(12) United States Patent
Thieme-Marti et al.

(10) Patent No.: US 11,273,327 B2
(45) Date of Patent: Mar. 15, 2022

(54) VIRTUAL BEAM'S-EYE VIEW IMAGING IN RADIATION THERAPY FOR PATIENT SETUP

(71) Applicant: Varian Medical Systems International AG, Palo Alto, CA (US)

(72) Inventors: Stefan Thieme-Marti, Windisch (CH); Andres Graf, Oberwil (CH); Christof Sidler, Lengnau (CH)

(73) Assignee: VARIAN MEDICAL SYSTEMS INTERNATIONAL AG

( * ) Notice: Subject to any disclaimer, the term of this patent is extended or adjusted under 35 U.S.C. 154(b) by 744 days.

(21) Appl. No.: 16/209,951

(22) Filed: Dec. 4, 2018

(65) Prior Publication Data

US 2019/0192881 A1 Jun. 27, 2019

Related U.S. Application Data

(60) Provisional application No. 62/608,973, filed on Dec. 21, 2017.

(51) Int. Cl.
*A61N 5/10* (2006.01)
*A61B 6/03* (2006.01)
*A61B 6/00* (2006.01)

(52) U.S. Cl.
CPC ............ *A61N 5/1069* (2013.01); *A61B 6/032* (2013.01); *A61B 6/4085* (2013.01); *A61N 5/103* (2013.01); *A61N 5/1049* (2013.01); *A61N 5/107* (2013.01); *A61N 5/1039* (2013.01); *A61N 2005/1056* (2013.01)

(58) Field of Classification Search
None
See application file for complete search history.

(56) References Cited

U.S. PATENT DOCUMENTS

| 2010/0119032 A1 | 5/2010 | Yan et al. | |
| 2016/0175617 A1* | 6/2016 | Pato | A61N 5/1071 600/1 |
| 2017/0361128 A1* | 12/2017 | Lachaine | G06K 9/6201 |

OTHER PUBLICATIONS

The Extended European Search Report, Application No. 18214849.4, dated Jun. 18, 2019.
The Extended European Search Report, Application No. 20200690.4, dated Mar. 9, 2021.

\* cited by examiner

*Primary Examiner* — Yi-Shan Yang
(74) *Attorney, Agent, or Firm* — Su IP Consulting

(57) ABSTRACT

A virtual beam's-eye view of a planning target volume is generated based on volumetric image data acquired immediately prior to radiation therapy by a radiation therapy system. The virtual beam's-eye view can then be displayed to confirm that, with the patient disposed in the current position, the planned beam-delivered treatment extends beyond the surface of the skin. In some embodiments, the virtual beam's-eye view can be displayed in conjunction with a beam's-eye view that is generated based on volumetric image data acquired during treatment planning, to create a blended beam's-eye view. In some embodiments, a field outline of a treatment beam can be superimposed on the blended beam's-eye view, thereby illustrating whether the planned beam-delivered treatment extends beyond the surface of the skin of the patient. The blended beam's-eye view can facilitate a manual confirmation process that verifies the planned beam-delivered treatment extends beyond the surface of the skin.

20 Claims, 7 Drawing Sheets

VIRTUAL BEAM'S-EYE VIEW IMAGING IN RADIATION THERAPY FOR PATIENT SETUP

CROSS-REFERENCE TO RELATED APPLICATION

The present application claims the benefit of U.S. Provisional Application No. 62/608,973, filed Dec. 21, 2017. The aforementioned U.S. Provisional Application, including any appendices or attachments thereof, is hereby incorporated by reference in its entirety.

BACKGROUND

Unless otherwise indicated herein, the approaches described in this section are not prior art to the claims in this application and are not admitted to be prior art by inclusion in this section.

Radiation therapy is a localized treatment for a specific target tissue (a planning target volume), such as a cancerous tumor. Ideally, radiation therapy is performed on the planning target volume that spares the surrounding normal tissue from receiving doses above specified tolerances, thereby minimizing risk of damage to healthy tissue. Prior to the delivery of radiation therapy, an imaging system is typically employed to provide a three dimensional image of the target tissue and surrounding area. From such imaging, the size and mass of the target tissue can be estimated and an appropriate treatment plan generated and target volume determined.

So that the prescribed dose is correctly supplied to the planning target volume (i.e., the target tissue) during radiation therapy, the patient should be correctly positioned relative to the linear accelerator that provides the radiation therapy. Typically, dosimetric and geometric data are checked before and during the treatment, to ensure correct patient placement and that the administered radiotherapy treatment matches the previously planned treatment. This process is referred to as image guided radiation therapy (IGRT), and involves the use of an imaging system to view target tissues while radiation treatment is delivered to the planning target volume. IGRT incorporates imaging coordinates from the treatment plan to ensure the patient is properly aligned for treatment in the radiation therapy device.

SUMMARY

In accordance with at least some embodiments of the present disclosure, a virtual beam's-eye view of a planning target volume is generated based on volumetric image data acquired immediately prior to radiation therapy by a radiation therapy system. The virtual beam's-eye view can then be displayed to confirm that, with the patient disposed in the current position, the planned beam-delivered treatment extends beyond the surface of the skin. In some embodiments, the virtual beam's-eye view can be displayed in conjunction with a beam's-eye view that is generated based on volumetric image data acquired during treatment planning, to create a blended beam's-eye view. In some embodiments, a field outline of a treatment beam can be superimposed on the blended beam's-eye view, thereby illustrating whether the planned beam-delivered treatment extends beyond the surface of the skin of the patient. Thus, the blended beam's-eye view can facilitate a manual confirmation process that verifies the planned beam-delivered treatment extends beyond the surface of the skin.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

The foregoing and other features of the present disclosure will become more fully apparent from the following description and appended claims, taken in conjunction with the accompanying drawings. These drawings depict only several embodiments in accordance with the disclosure and are, therefore, not to be considered limiting of its scope. The disclosure will be described with additional specificity and detail through use of the accompanying drawings.

DETAILED DESCRIPTION

Figure 1:
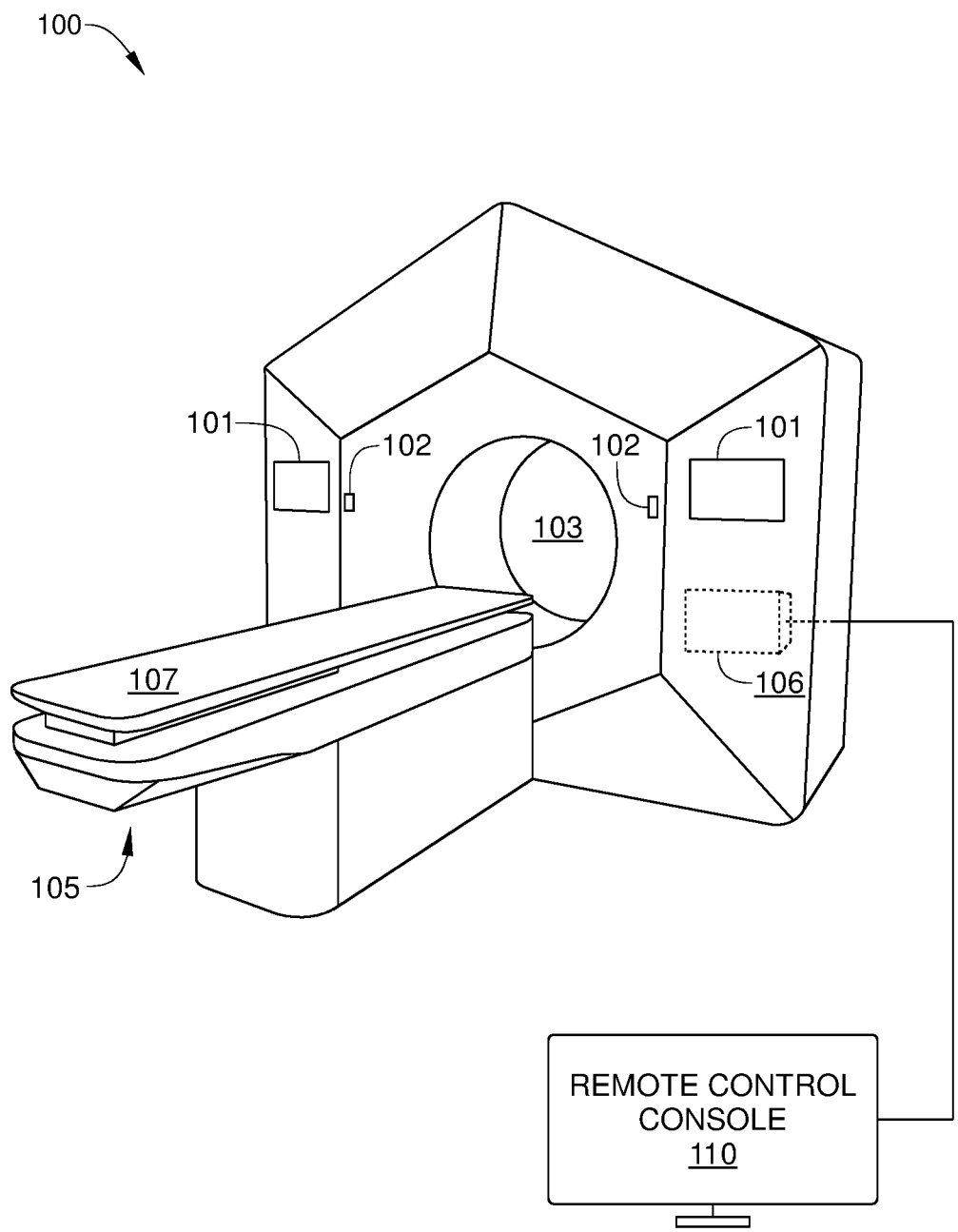
FIG. 1 is a perspective view of a radiation therapy system, according to one or more embodiments of the present disclosure.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the disclosure, as generally described herein, and illustrated in the figures, can be arranged, substituted, combined, and designed in a wide variety of different configurations, all of which are explicitly contemplated and make part of this disclosure.

When the tumor or clinical target volume is disposed near the surface of the skin, correct dosing of the specific target tissue, or the "planning target volume," can be problematic. Consequently, a virtual bolus, sometimes referred to as a "skin flash region," is employed in IGRT to ensure that the beam delivering treatment extends beyond the surface of the skin and the dosing of the planning target volume is accurate. For visualization of the skin flash region immediately prior to treatment, a beam's-eye view X-ray image is often generated for patient setup, in which a high-energy film is exposed to an X-ray source, such as the treatment beam itself or some lower energy X-ray beam. Because the X-rays employed to generate the beam's-eye view image mimic the path of the treatment beam during dosing, the beam's eye view enables a radiation therapist to ensure that the relative orientation and position of the patient and the treatment beam are correct. Alternatively, a field light can be employed for visualization of the skin flash region. With a field light, visible light that is coincident with the path of the treatment beam illuminates the planning target volume, and provides visual confirmation that the treatment beam extends beyond the surface of the skin.

However, these conventional approaches have multiple drawbacks. First, checking the skin flash region using a field light is time consuming, and requires a therapist to enter the treatment room and then return to the console area. In addition, some radiation therapy systems do not even include a field light. Second, setup images taken in the beam direction (i.e., beam's eye view images) can be difficult to use to verify the planned treatment area. Due to the unusual viewing angle of beam's-eye view images, matching the newly acquired beam's-eye view image to a previously acquired reference image is not a visually simple task. Third, the generation of beam's-eye view images requires additional patient dosing and time. Fourth, given the none-rigid nature of certain anatomy such as the breast, the current rigid matching based on cone-beam computed tomography (CBCT) in transversal, frontal, and sagittal display is not practical for setup.

In light of the above, there is a need in the art for improved systems and techniques for confirming that beam-delivered treatment in radiation therapy extends beyond the surface of the skin and accurately doses the planning target volume.

In image guided radiation therapy (IGRT), a manual or automatic matching process ensures that the relative orientation and position of the patient and the treatment beam are correct immediately before dosing by the treatment beam takes place. In the matching process, digitally constructed 2D views of the planning target volume are generated from digital volume data taken during the treatment planning process and from digital volume data acquired at the time of treatment; matching of the treatment planning 2D views and the time-of-treatment 2D views enables accurate positioning of the patient immediately prior to treatment. According to embodiments of the present disclosure, a virtual beam's eye view (BEV) image of the planning target volume is also generated from the digital volume data acquired at the time of treatment, so that the virtual BEV image can be employed in the matching process by the radiation therapist. Specifically, prior to delivery of planned radiation therapy, a virtual BEV image is displayed to a radiation therapist as part of an image match verification tool. The virtual BEV image can be a digitally reconstructed radiograph (DRR) projection image constructed from the point of view of the treatment beam at a certain point during the planned radiation treatment. Alternatively or additionally, the virtual BEV image can be a virtual 2D slice, where the slice is taken through the planning target volume and positioned orthogonal to the treatment beam. By viewing the virtual BEV image (or one or more virtual slices), the therapist can perform a matching process on a planning target volume without entering the treatment room for visual confirmation that a skin flash region is indicated by a field light. In addition, the patient is not dosed with additional radiation through the generation of a BEV X-ray image. Instead, the virtual BEV image employed in the match process is generated from image data that are already acquired as part of a radiation therapy workflow, such as CBCT. A radiation therapy system on which such a radiation therapy workflow can be performed is illustrated in FIG. 1.

FIG. 1 is a perspective view of a radiation therapy system 100, according to one or more embodiments of the present disclosure. Radiation therapy (RT) system 100 is configured to provide stereotactic radiosurgery and precision radiotherapy for lesions, tumors, and conditions anywhere in the body where radiation treatment is indicated. As such, RT system 100 can include one or more of a linear accelerator (LINAC) that generates a megavolt (MV) treatment beam of high energy X-rays, a kilovolt (kV) X-ray source, an X-ray imager, and, in some embodiments, an MV electronic portal imaging device (EPID) (not shown for clarity). By way of example, radiation therapy system 100 configured with a circular gantry is described herein. Any other suitable radiation therapy system can also benefit from and be configured to implement the embodiments described herein, such as a radiation therapy system configured with a C-arm gantry.

Generally, RT system 100 is capable of MV and kV imaging techniques, to enable the treatment planner and physician to make clinical decisions that are most appropriate for the patient based on the anatomy of the patient. In some situations, a treatment plan can include kV imaging for improved visualization of soft tissue. In addition, iterative cone beam computed tomography (iCBCT) enhances image reconstruction and can further improve visualization of soft tissue in the kV images.

RT system 100 may include one or more touchscreens 101, couch motion controls 102, a bore 103, a base positioning assembly 105, a couch 107 disposed on base positioning assembly 105, and an image acquisition and treatment control computer 106, all of which are disposed within a treatment room. RT system 100 further includes a remote control console 110, which is disposed outside the treatment room and enables treatment delivery and patient monitoring from a remote location. Base positioning assembly 105 is configured to precisely position couch 107 with respect to bore 103, and motion controls 102 include input devices, such as button and/or switches, that enable a user to operate base positioning assembly 105 to automatically and precisely position couch 107 to a predetermined location with respect to bore 103. Motion controls 102 also enable a user to manually position couch 107 to a predetermined location. In some embodiments, RT system 100 further includes one or more cameras (not shown) in the treatment room for patient monitoring.

Figure 2:
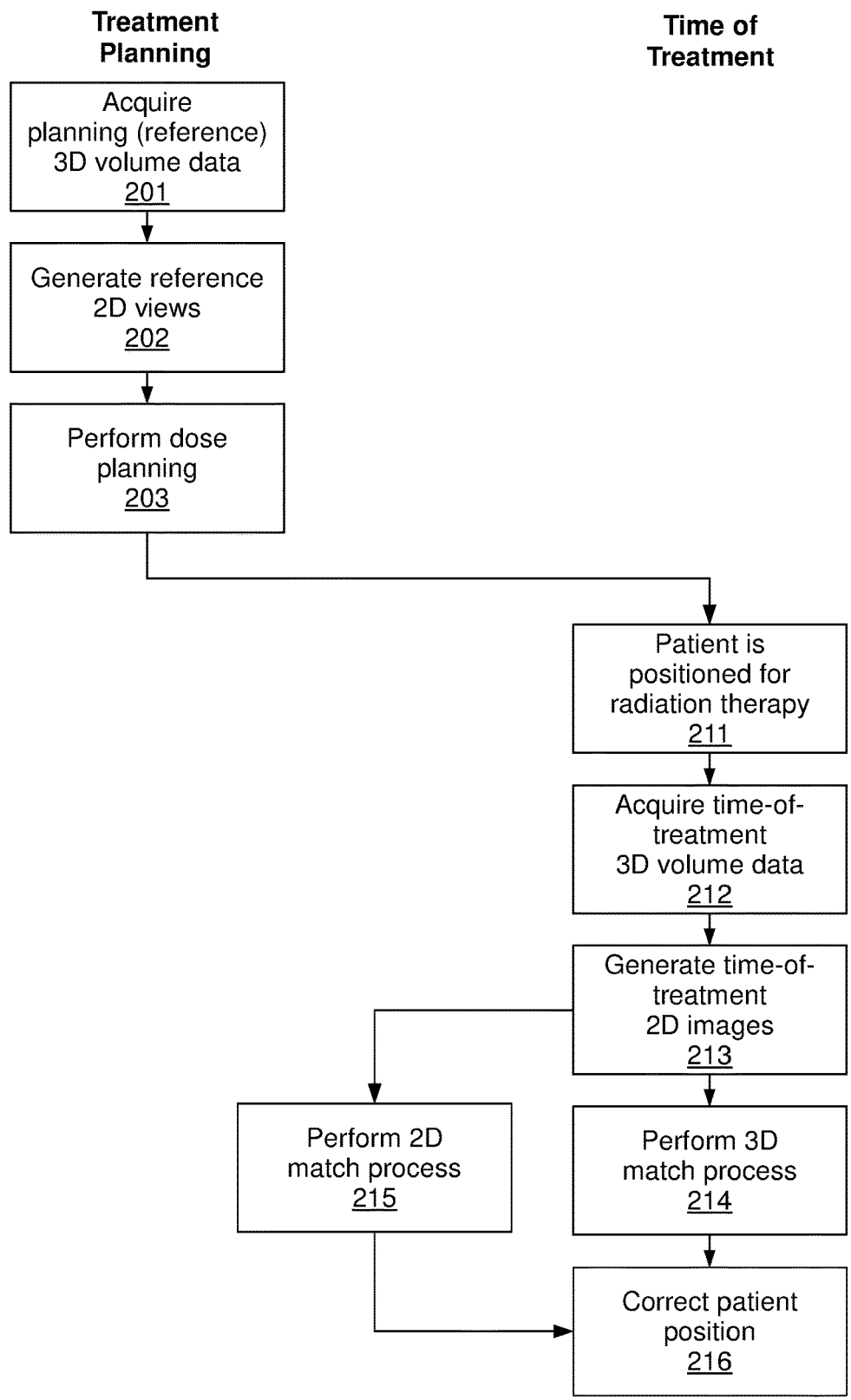
FIG. 2 is a conceptual block diagram illustrating an image guided radiation therapy (IGRT) process, according to various embodiments of the current disclosure.

FIG. 2 is a conceptual block diagram illustrating a radiation therapy workflow, according to various embodiments of the present disclosure. Steps 201-203 take place during a treatment planning phase, in which dosimetry planning for a particular patient is performed. Steps 211-216 take place at the time of treatment, i.e., while the patient is positioned on the couch of the radiation therapy system at a time subsequent to the planned treatment phase. In some embodiments, the treatment planning phase is also performed on an imaging system that is different from RT system 100.

In step 201, planning 3D volume data (hereinafter referred to as "reference 3D volume data") are acquired. In some embodiments, scanning software collects and reconstructs the planning 3D volume data. That is, the scanning software produces a so-called "digital volume" composed of three-dimensional voxels of anatomical data that can then be manipulated and visualized with appropriate software. For example, the patient is positioned in RT system 100, or another suitable X-ray imaging system, and the 3D planning volume data is generated by, for example, CBCT. The reference 3D volume data includes volumetric reference image information and, when produced by the CBCT process, can include hundreds of distinct digital X-ray images. Alternatively or additionally, the 3D planning volume data can include volumetric image data generated by any other suitable medical imaging technology that can be employed to identify target tissues in radiation therapy planning and IGRT, such as computed tomography (CT), positron emission tomography (PET), ultrasound imaging, magnetic resonance imaging (MRI), or any combination thereof.

In step 202, reference 2D views of the planning target volume and surrounding anatomy are generated based on the reference 3D volume data. Such reference 2D views can be used to visualize the planning target volume. Because RT system 100 generally performs alignment of couch 107 in three orthogonal planes (e.g., axial, sagittal, and coronal), for each of these three orthogonal planes, a plurality of reference 2D views (virtual slices) that are parallel to the plane are generated in step 202. For example, to enable comprehensive visualization of the planning target volume along an axis perpendicular to the sagittal plane, a plurality of virtual slices are typically generated at different locations along such an axis. Similarly, to enable comprehensive visualization of the planning target volume along an axis perpendicular to the axial plane and to the coronal plane, a plurality of virtual slices is typically generated at different locations along the axis perpendicular to the axial plane and at different locations along the axis perpendicular to the coronal plane. Alternatively, in some embodiments, the above-described reference 2D views of the planning target volume are generated at the time of treatment using the reference 3D volume data.

In step 203, dosimetry planning is performed based on the reference 3D volume data generated in step 201, and the planning target volume to be radiated is determined.

In step 211, which occurs at the time of treatment, the patient is positioned for radiation therapy on couch 107 of RT system 100 (shown in FIG. 1), for example using marks on the patient's skin that are aligned with treatment room alignment lasers.

In step 212, time-of-treatment 3D volume data are acquired. Scanning software running on image acquisition and treatment control computer 106 (shown in FIG. 1) collects and reconstructs the time-of-treatment 3D volume data. Thus, a digital volume is produced of the planning target volume of the patient at the time of treatment.

In step 213, time-of-treatment 2D views of the planning target volume and surrounding anatomy (hereinafter referred to as "time-of-treatment 2D views") are generated based on the time-of-treatment 3D volume data acquired in step 212. The time-of-treatment 2D views generated in step 213 include a plurality of virtual slices that are parallel to each of the axial, sagittal, and coronal planes. The time-of-treatment 2D virtual slices that are parallel to each of the axial, sagittal, and coronal planes can be subsequently used to assess quality assurance of the treatment plan and precisely align the patient prior to radiation treatment by comparing patient anatomical structures shown in the reference 2D virtual slices to the time-of-treatment 2D virtual slices. As noted above, in some embodiments, instead of being generated in step 202, such reference 2D virtual slices can be generated at time-of-treatment (e.g., in step 213) based on the reference 3D volume data acquired in step 201.

In addition, according to some embodiments, the time-of-treatment 2D views generated in step 213 include a virtual BEV image and/or BEV-oriented virtual slices. Unlike the time-of-treatment 2D virtual slices that are parallel to each of the axial, sagittal, and coronal planes, the virtual BEV image and/or BEV-oriented virtual slices are well-suited to verify that the treatment beam extends past the skin of the patient. It is noted that the time-of-treatment virtual BEV image and BEV-oriented virtual slices are generated from time-of-treatment 3D volume data acquired in step 212, and no additional acquisition time or dosing are needed. The time-of-treatment virtual BEV image and BEV-oriented virtual slices are described in greater detail below in conjunction with FIGS. 3 and 4.

In step 214, an automated 3D matching process is performed. In the automated match process, RT system 100 performs the matching of time-of-treatment 3D volume data acquired in step 212 to corresponding reference 3D volume data generated in step 201. For example, CBCT information acquired in step 201 and CBCT information acquired in step 212 are compared. RT system 100 then determines couch adjustments required to align the patient and planning target volume with the actual dosing location.

In step 215, the time-of-treatment 2D views generated in step 213 are registered with the reference 2D views, i.e., a 2D matching process is performed. As part of the matching process, discrepancies between the position of anatomical structures in the reference 2D views and in the time-of-treatment 2D views are detected. Corrections to the patient setup position are then determined. For example, couch shift parameters can be calculated for positioning the actual location of patient anatomy relative to the radiation isocenter of RT system 100. Specifically, the couch shift parameters are calculated so that the actual location of patient anatomy at the time-of-treatment coincides with the position of patient anatomy in the reference 2D images.

In some embodiments, the match process performed by the therapist is a manual match process. In such a manual match process, the therapist can merge, overlay, blend, or otherwise compare the time-of-treatment 2D views and the reference 2D views of the three orthogonal views. In addition, according to embodiments of the present disclosure, in such a manual match process, the therapist can merge, overlay, blend, or otherwise compare a time-of-treatment virtual BEV image and/or time-of-treatment BEV-oriented virtual slice with a reference BEV image or virtual slice. In such embodiments, the time-of-treatment virtual BEV image (or time-of-treatment BEV-oriented virtual slice) is based on the volumetric time-of-treatment image information of the planning target volume and the reference virtual BEV image (or reference BEV-oriented virtual slice) is constructed based on the volumetric reference image information of the planning target volume. Since the time-of-treatment virtual BEV image and the reference BEV image can both be projection images of the planning target volume along the same specific viewing angle, a radiation therapist can visually perform a manual matching or alignment of the two images when displayed together in a blended fashion, i.e., in a "blended view." When field outlines of the treatment beam are overlayed on such a blended view, the radiation therapist can then readily confirm that a treatment beam extends beyond the skin of the patient. In this way, dosing of the radiation therapy will be accurate. Alternatively, in some embodiments, field outlines of the treatment beam can be overlayed on the virtual BEV instead of the blended view.

Alternatively or additionally, in some embodiments, the match process performed by the therapist is a verification of the results of the automated match process performed in step 214. In an automated match process, RT system 100 determines couch adjustments required to align the patient and planning target volume with the actual dosing location. Thus, in such embodiments, the radiation therapist visually confirms that the automated match process has accurately aligned the planning target volume with the dosing location of RT system 100. This visual confirmation can be via comparison, merging, or blending of the time-of-treatment 2D views generated in step 213 and the reference 2D views generated in step 202. In addition, the visual confirmation includes the comparison, merging, or blending of a time-of-treatment virtual BEV image (or virtual slice) with a reference BEV image. Alternatively or additionally, the visual confirmation includes the comparison, merging, or blending of time-of-treatment BEV-oriented virtual slices generated from the time-of-treatment 3D volume data with reference BEV-oriented virtual slices generated from the reference 3D volume data. For example, the virtual BEV image (generated based on the time-of-treatment 3D volume data) can be displayed together with a reference BEV image that is generated based on the reference 3D volume data of the planning target volume.

During the treatment phase, it is necessary to place the patient under the particle accelerator of RT system 100 exactly as considered in the dosimetry planning stage. Therefore, in step 216, the calculated shift parameters are implemented by base positioning assembly 105 to reposition couch 107 so that the actual location of patient anatomy at the time-of-treatment coincide with the position of that anatomy in the reference 2D images (base positioning assembly 105 to reposition couch 107 are shown in FIG. 1). Delivery of treatment can then begin.

In some embodiments, the matching process of step 215 and the correction of the patient setup position of step 216 is performed by the radiation therapist using an image verification tool displayed on remote control console 110 (shown in FIG. 1). One example of such a match verification tool is illustrated in FIG. 3.

Figure 3:
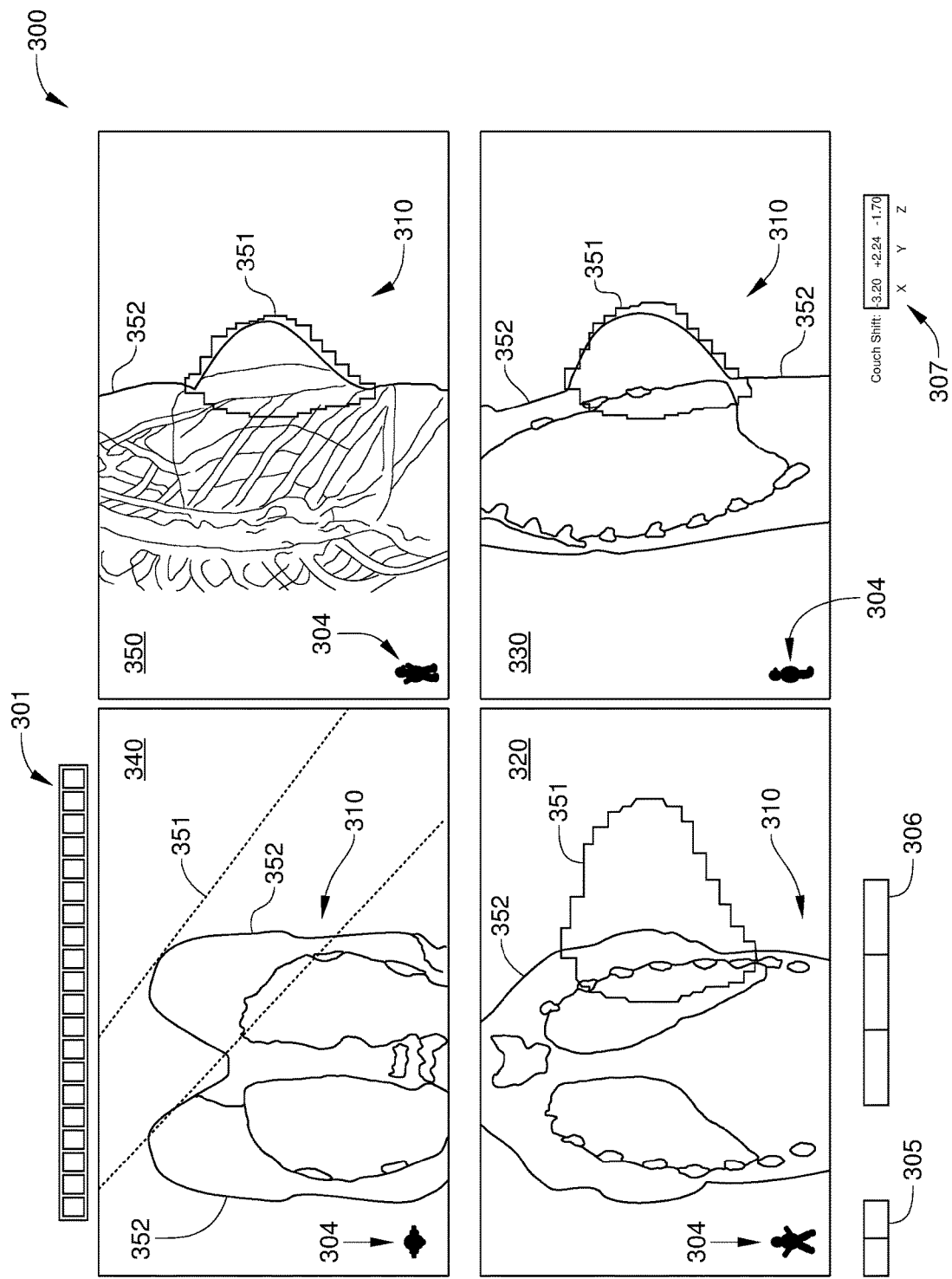
FIG. 3 illustrates a match verification tool that facilitates calculation of shift parameters for a base positioning assembly to automatically position a couch of the radiation therapy system of FIG. 1, according to an embodiment of the disclosure.

FIG. 3 illustrates a match verification tool 300 that facilitates calculation of shift parameters for base positioning assembly 105 to automatically position couch 107, according to an embodiment of the disclosure. As shown, match verification tool 300 includes imaging tools 301, patient orientation indicators 304, a taskbar 305, multiple action buttons 306, and a couch shift indicator 307. Imaging tools 301 enable a radiation therapist to change the display of the images in various ways. For example, one such tool may apply filters that improve image quality and facilitate matching of images and/or verification of matched images. Another such tool is a blending slider for comparing the position of patient anatomy in a reference image and in an acquired image. Patient orientation indicators 304 indicate the anatomical position and relative relationship of an image to anatomical nomenclature in each view window of match verification tool 300. Taskbar 305 provides options for selecting the imaging mode and a particular matching technique to be employed by RT system 100 and/or by the radiation therapist. The multiple action buttons 306 variously apply the calculated shift to the position of couch 107, enable resetting of changes, perform adjustments to the match, cancel the current match, and reacquire a setup image, among other functions. Couch shift indicator 307 displays the distance each couch axis should move to correctly position the patient for treatment. As noted above, match results generated by RT system 100 can include values displayed by couch shift indicator 307. In addition, when a radiation therapist adjusts the matching between a reference image and a time-of-treatment setup image, the couch shift values displayed by shift indicator 307 are updated.

In addition, match verification tool 300 includes a coronal (or frontal) plane view 320, a sagittal plane view 330, an axial plane view 340, and a virtual BEV window 350. Thus, in the embodiment illustrated in FIG. 3, match verification tool 300 allows reference and time-of-treatment images to be matched in four views. Coronal plane view 320 enables the display and matching of reference 2D images and time-of-treatment 2D images in a coronal view (i.e., a view along an axis perpendicular to the coronal plane), sagittal plane view 330 enables the display and matching of reference 2D images and time-of-treatment 2D images in a sagittal view, and axial plane view 340 enables the display and matching of reference 2D images and time-of-treatment 2D images in an axial view. Furthermore, virtual BEV window 350 enables the display and matching of reference 2D views and time-of-treatment 2D views in a beam's-eye view (i.e., a view along an axis parallel to a specific path of the planned treatment beam).

For the reference 2D views and time-of-treatment 2D views displayed in coronal plane view 320, sagittal plane view 330, or axial plane view 340, the image plane is considered the physical plane corresponding to the location of the 2D virtual slice. For virtual BEV images displayed by virtual BEV window 350, the image plane is considered the projection plane of the virtual BEV image.

It is noted that virtual BEV window 350 is configured to display reference 2D BEV views and time-of-treatment 2D BEV views for any beam angle of the planned treatment beam. By contrast, each of coronal plane view 320, sagittal plane view 330, and axial plane view 340, is configured to display reference 2D images and time-of-treatment 2D images from a single fixed point of view (or viewing angle). Thus, the image plane for each reference 2D image or time-of-treatment 2D image displayed in, for instance, sagittal plane view 330 is parallel with the image plane of any other reference 2D view or time-of-treatment 2D view displayed in sagittal plane view 330, while the image plane for each 2D BEV view displayed by virtual BEV window 350 is generally not parallel with the image plane of other 2D BEV images displayed by virtual BEV window 350.

Each of coronal plane view 320, sagittal plane view 330, axial plane view 340, and virtual BEV window 350 displays a portion of patient anatomy 310. In coronal plane view 320, sagittal plane view 330, axial plane view 340, patient anatomy 310 is displayed as a 2D image, which is a virtual slice through patient anatomy 310. By contrast, in embodiments in which virtual BEV window 350 displays a projected DRR image, patient anatomy is shown as a virtual projected view in virtual BEV window 350, simulating a conventional X-ray image. Alternatively or additionally, in some embodiments, virtual BEV window 350 can display a 2D virtual slice of patient anatomy instead of a projected DRR image, where the 2D virtual slice is positioned along and perpendicular to a particular planned path of the treatment beam. In either case, the image displayed in virtual BEV window 350 has an image plane that is perpendicular to a path of a particular planned treatment beam that passes through the image plane.

In some embodiments, some or all of coronal plane view 320, sagittal plane view 330, axial plane view 340, and virtual BEV window 350 can be selected to display a time-of-treatment 2D image of patient anatomy 310, a reference 2D image of patient anatomy, a time-of-treatment 2D image superimposed on a reference 2D image, or a blended view of patient anatomy 310, in which a radiation therapist can simultaneously view a reference 2D image and a time-of-treatment 2D image. In the blended view, the radiation therapist can employ one of imaging tools 301 to enable a slider function that facilitates comparison and matching of a reference 2D image and a time-of-treatment 2D image. For example, a slider tool included in imaging tools 301 can be activated that enables the comparison, at a selected location, of a reference 2D image and a corresponding time-of-treatment 2D image. Thus, when the slider tool is activated for a window displaying a view of a particular planar slice of a planning target volume (e.g., a view toward one of the axial, sagittal, or coronal planes), actuation of the slider selects a reference image (2-D slice) and a corresponding time-of-treatment image (2-D slice) at a specific planar location.

According to embodiments of the disclosure, virtual BEV window 350 can be used to verify that the treatment beam extends past the skin for any selected beam angle of the treatment beam that is programmed to occur during treatment. Specifically, match verification tool 300 is configured to display, when an appropriate imaging tool 301 is selected (e.g., a field outlines tool), the extents 351 of the planned treatment beam relative to the anatomy of the patient. In the embodiment illustrated in FIG. 3, extents 351 of the planned treatment beam are displayed in each of coronal plane view 320, sagittal plane view 330, axial plane view 340, and virtual BEV window 350. However, when only viewing coronal plane view 320, sagittal plane view 330, and axial plane view 340, visually determining the location of extents 351 of the planned treatment beam relative to surface 352 of patient skin in these views can be unreliable and/or time-consuming. By contrast, in virtual BEV window 350, surface 352 of patient skin relative to extents 351 of the planned treatment beam is readily determined visually for any angle of the planned treatment, due to the positioning of the image plane for views shown in virtual BEV window 350. One embodiment of an image plane for a view displayed in sagittal plane view 330 is shown in FIG. 4A, one embodiment of an image plane for a view displayed in virtual BEV window 350 is shown in FIG. 4B, and one embodiment of an image plane for a 2D projected view displayed in virtual BEV window 350 is shown in FIG. 4C.

Figure 4A:
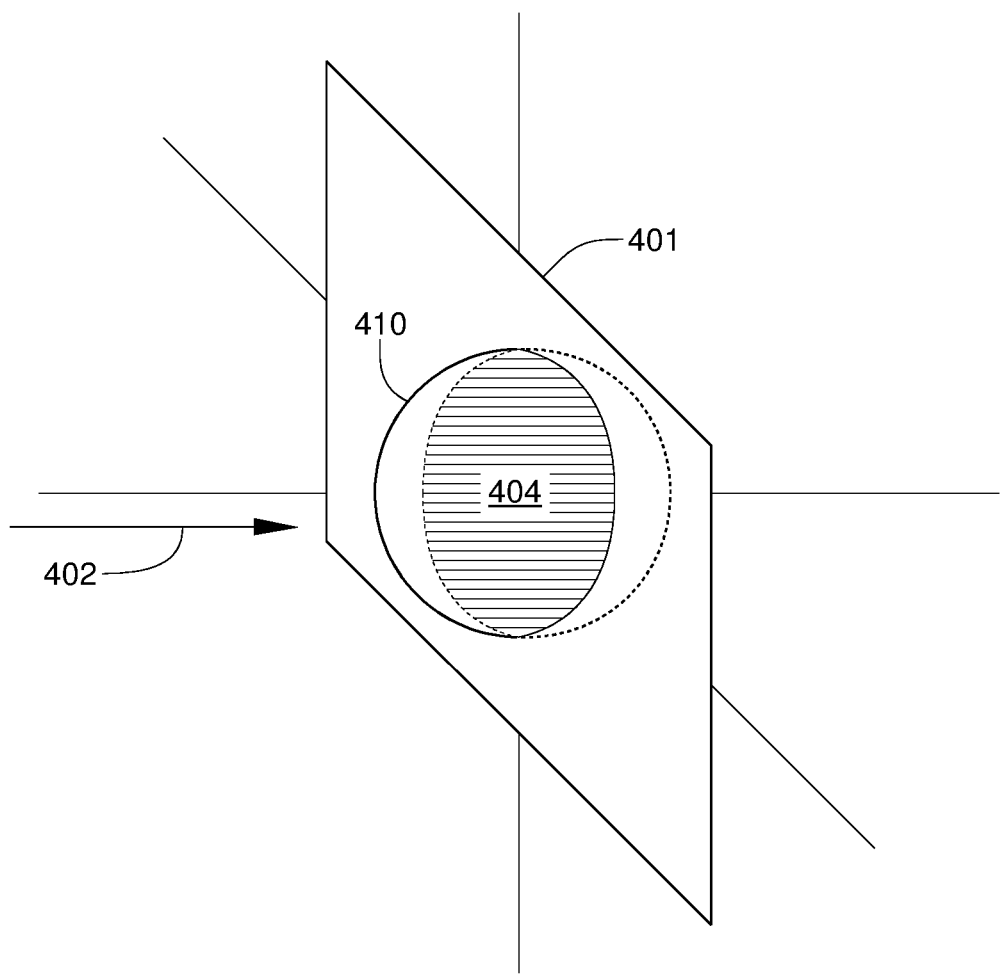
FIG. 4A illustrates an image plane for a view displayed in the sagittal plane view of FIG. 3, according to an embodiment of the disclosure.

FIG. 4A schematically illustrates an image plane 401 for a 2D view displayed in, for example, sagittal plane view 330 of FIG. 3, according to an embodiment of the disclosure. The 2D view being displayed can be a reference 2D view of a planning target volume 410, a time-of-treatment 2D view of the planning target volume 410, or a blended 2D view that includes a reference 2D view and a corresponding time-of-treatment 2D view of the planning target volume 410. As shown, image plane 401 for the 2D view being displayed passes through planning target volume 410 and corresponds to the location of the 2D virtual slice being displayed in sagittal view 330. Further, image plane 401 is perpendicular to a virtual viewing direction 402. As a result, a 2D slice 404 (cross-hatched area of planning target volume 410) that is parallel to the sagittal plane and perpendicular to virtual viewing direction 402 is displayed in sagittal plane view 330 of FIG. 3. Similarly, an image plane (not shown) for the 2D view being displayed in axial plane view 340 corresponds to the location of a 2D virtual slice that passes through planning target volume 410, is perpendicular to a virtual viewing direction, and is displayed in axial plane view 340. Furthermore, an image plane (not shown) for the 2D view being displayed in coronal plane view 320 corresponds to the location of a 2D virtual slice that passes through planning target volume 410, is perpendicular to a virtual viewing direction, and is displayed in coronal plane view 320.

Figure 4B:
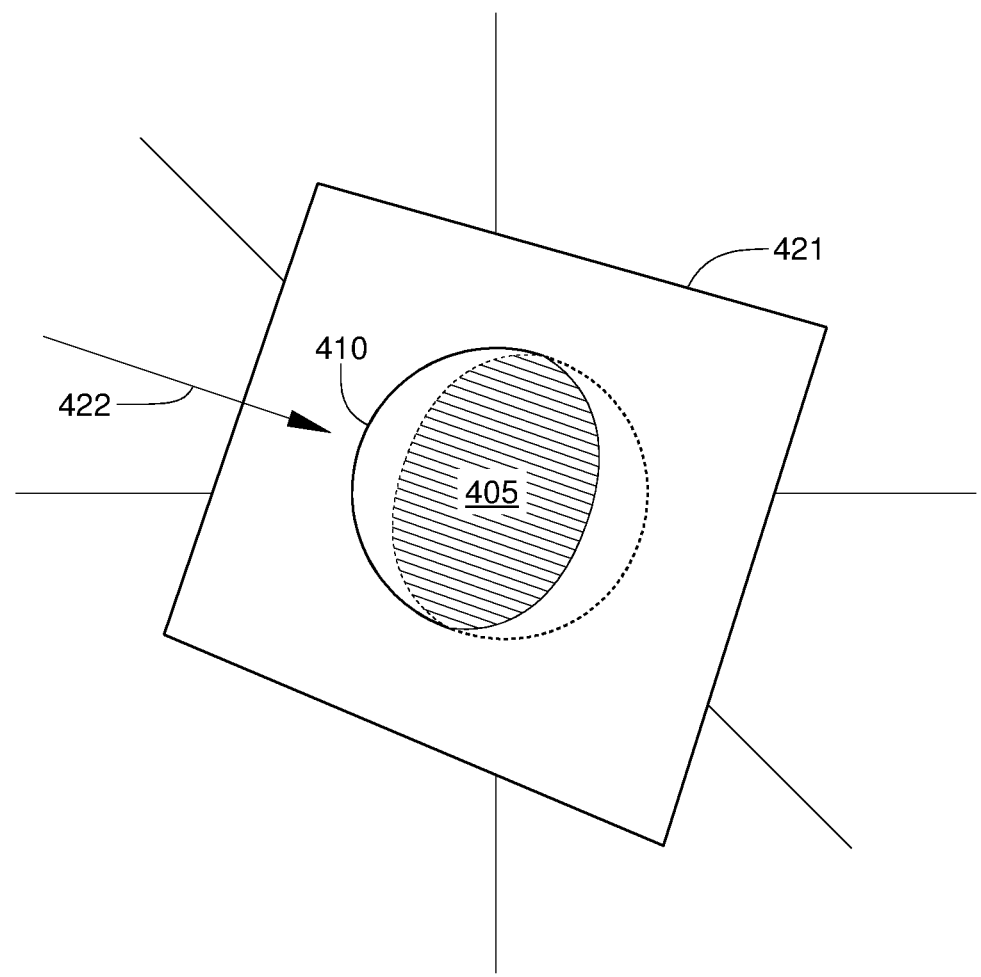
FIG. 4B illustrates an image plane for a view displayed in the virtual beam's-eye view window of FIG. 3, according to an embodiment of the disclosure.

FIG. 4B schematically illustrates an image plane 421 for a 2D view displayed in virtual BEV window 350 of FIG. 3, according to an embodiment of the disclosure. The 2D view being displayed in virtual BEV window 350 is represented by the cross-hatched region 405, and can be a reference 2D BEV slice of planning target volume 410, a time-of-treatment 2D BEV slice of the planning target volume 410, or a blended 2D BEV slice that includes a reference 2D BEV slice and a corresponding time-of-treatment 2D BEV slice of the planning target volume 410. As shown, image plane 421 for the 2D view displayed in virtual BEV window 350 passes through planning target volume 410 and corresponds to the location of the 2D BEV view being displayed in virtual BEV window 350. Further, image plane 421 is perpendicular to a virtual viewing direction that is coincident with a planned treatment beam path 422. In contrast to image plane 401 depicted in FIG. 4A, image plane 421 is generally not parallel to a coronal plane, a sagittal plane, or an axial plane associated with RT treatment of planning target volume 410. Instead, image plane 421 is perpendicular to planned treatment beam path 422 that passes through planning target volume 410. It is noted that planned treatment beam path 422 can be the path of a treatment beam at any portion of a particular RT treatment of planning target volume 410. For example, in a volumetric modulated arc therapy (VMAT) treatment of planning target volume 410, planned treatment beam path 422 of the treatment beam is continuously changing over time during delivery of radiation therapy. Alternatively or additionally, planned treatment beam path 422 can be the path of any other treatment beam path for treatment of planning target volume 410.

Figure 4C:
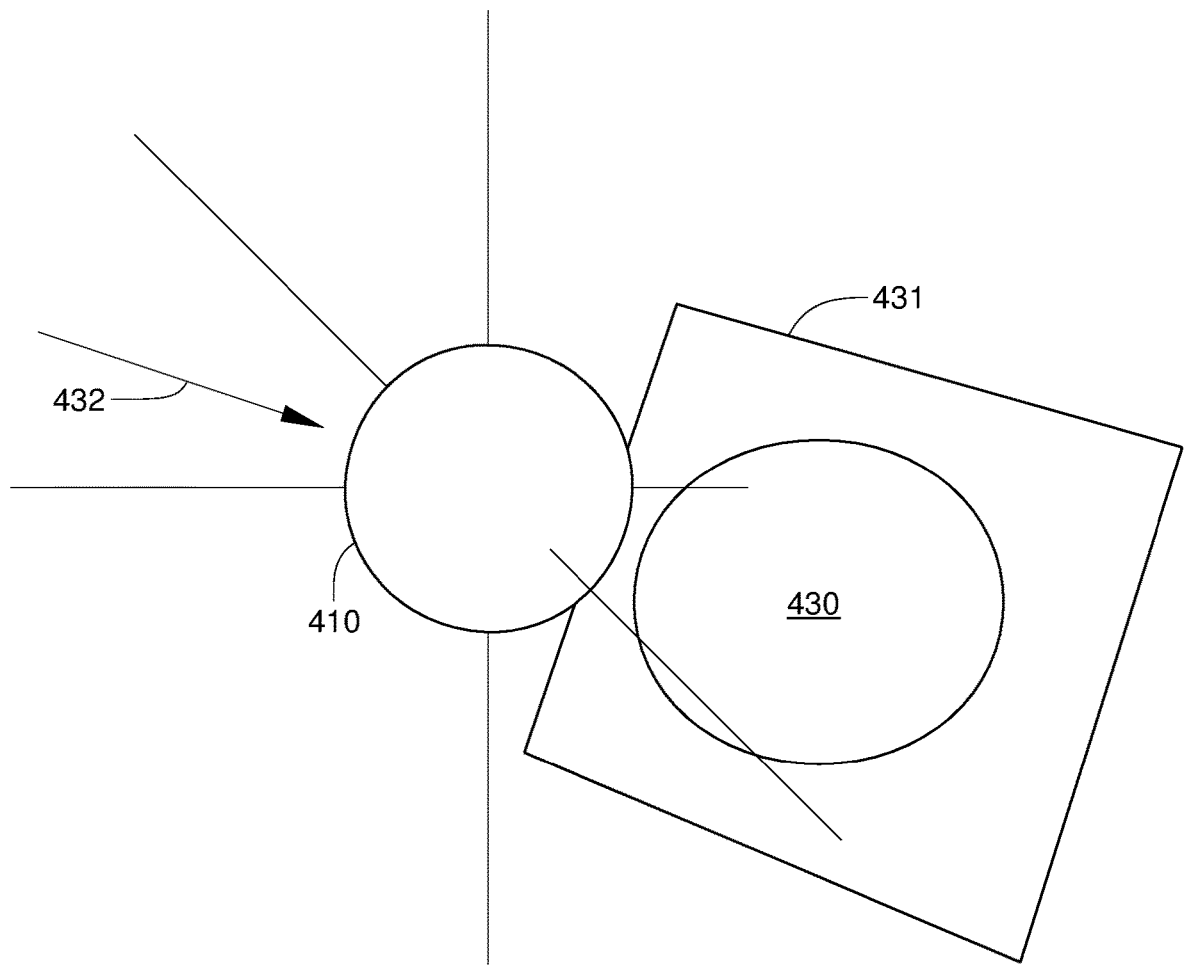
FIG. 4C illustrates an image plane for a 2D projected view displayed in the virtual beam's-eye view window of FIG. 3, according to an embodiment of the disclosure.

FIG. 4C schematically illustrates an image plane 431 for a 2D projected view 430 displayed in virtual BEV window 350 of FIG. 3, according to an embodiment of the disclosure. In the embodiment illustrated in FIG. 4C, 2D projected view 430 being displayed in virtual BEV window 350 can be a reference DRR of planning target volume 410, a time-of-treatment DRR of the planning target volume 410, or a blended DRR BEV that includes a reference DRR BEV and a corresponding time-of-treatment DRR BEV of the planning target volume 410. As shown, image plane 431 for 2D projected view 430 corresponds to the projection plane that is employed in generating the above DDR BEVs of the planning target volume 410. Thus, in such embodiments, image plane 431 for 2D projected view 430 does not pass through planning target volume 410, but is perpendicular to a planned treatment beam path 432.

Figure 5:
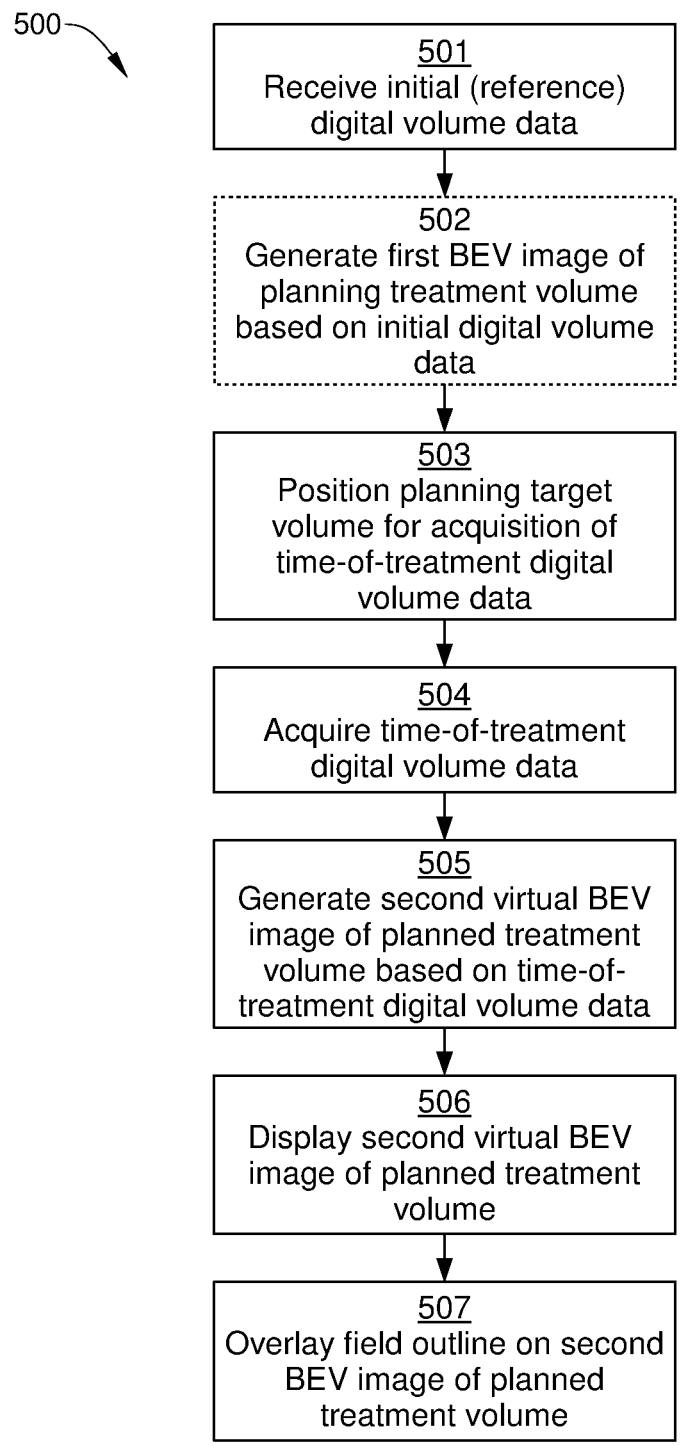
FIG. 5 sets forth a flowchart of an example method for viewing a planning target volume for radiation therapy, according to one or more embodiments of the present disclosure.

FIG. 5 sets forth a flowchart of an example method for viewing a planning target volume for radiation therapy, according to one or more embodiments of the present disclosure. The method may include one or more operations, functions, or actions as illustrated by one or more of blocks 501-508. Although the blocks are illustrated in a sequential order, these blocks may be performed in parallel, and/or in a different order than those described herein. Also, the various blocks may be combined into fewer blocks, divided into additional blocks, and/or eliminated based upon the desired implementation. Although the method is described in conjunction with the systems of FIGS. 1-4C, persons skilled in the art will understand that any suitably configured radiation therapy system is within the scope of the present disclosure.

A method 500 begins at step 501, in which a computing device associated with RT system 100 (such as image acquisition and treatment control computer 106) receives initial digital volume data of a planning target volume. The digital volume data can include sets of images, where each set includes a plurality of image slices taken through the planning target volume and surrounding anatomy. The plurality of image slices are taken orthogonal to a single viewing direction, so that the image slices included in one set are parallel to one of axial, sagittal, or coronal planes. In some embodiments, the digital volume data can include one or more reference 2D BEV images that each include an image plane that is perpendicular to a planned treatment beam path that passes through that image plane. Alternatively or additionally, the digital volume data can include a set of 2D BEV virtual slices that each include an image plane that is perpendicular to a planned treatment beam path that passes through the image plane.

In optional step 502, the computing device generates a first 2D view of the planning target volume based on the initial digital volume data. Specifically, the computing device generates one or more virtual BEV images of the planning target volume, based on the initial digital volume data generated prior to radiation therapy. The one or more BEV images are also generated to appear to be taken from the direction of the treatment beam and from the point of view of the source of the treatment beam. The first 2D view has a first image plane that is perpendicular to a planned treatment beam path that passes through the image plane. In embodiments in which the initial digital volume data includes such a 2D view of the planning target volume, step 502 is not performed.

In step 503, the planning target volume is positioned for acquisition of time-of-treatment digital volume data of the planning target volume. That is, the patient associated with the initial digital volume data is positioned on couch 107 of RT system 100 so that the planning target volume is located as close as possible to the planned treatment isocenter.

In step 504, the computing device causes RT system 100 to acquire time-of-treatment digital volume data of the planning target volume. For example a CBCT process may be performed by RT system 100.

In step 505, the computing device generates a second 2D view of the planning target volume based on the time-of-treatment digital volume data. Thus, the computing device generates one or more virtual BEV images of the planning target volume, based on the time-of-treatment digital volume data acquired in step 504, and also on a planned treatment that includes at least one treatment beam. The one or more virtual BEV images (time-of-treatment virtual BEV images) are generated to appear to be taken from the direction of the treatment beam and from the point of view of the source of the treatment beam. Any suitable DRR generation algorithm or other software for processing digital volume data can be employed in step 505 to generate such virtual BEV images.

In step 506, the computing device causes a time-of-treatment virtual BEV image that is generated in step 505 to be displayed in a blended view, for example on remote control console 110. Step 506 may be performed in response to a user input selecting a particular virtual BEV image to be displayed. For example, the user may perform the input via a suitable imaging tool 301. In some embodiments, the time-of-treatment virtual BEV image that is displayed in step 506 is displayed without a corresponding reference virtual BEV image. In other embodiments, the time-of-treatment virtual BEV image that is displayed in step 506 is displayed superimposed on a corresponding reference virtual BEV image. In other embodiments, the time-of-treatment virtual BEV image that is displayed in step 506 is displayed in a blended view, which includes the time-of-treatment virtual BEV image and the corresponding reference virtual BEV image. Thus, the blended view includes a virtual BEV image that is generated based on time-of-treatment digital volume data and a virtual BEV image that is generated based on reference digital volume data.

In step 507, the computing device determines a field outline for the treatment beam included in the planned treatment. The field outline is determined based on the particular time-of-treatment virtual BEV image that is selected in step 506 and a corresponding treatment beam and treatment beam angle. The treatment beam angle is that angle associated with the treatment beam when the treatment beam is applied to the planning target volume, passes through the image plane of the selected virtual BEV image, and is perpendicular to the image plane of the selected virtual BEV image.

In step 508, the computing device causes the field outline to be displayed with the virtual BEV image displayed in step 505. That is, the field outline is superimposed on the virtual BEV image(s) displayed in step 505. In some embodiments, anatomical structures associated with the planning target volume are also overlayed on the blended view. It is noted that virtual BEV window 350 displays a projection image of patient anatomy 310 that is a virtual BEV image from whatever viewing angle is requested by the radiation therapist. Generally, the viewing angle used to generate the 2D virtual BEV image corresponds to the angle of the treatment beam or beams employed in the current treatment plan. Consequently, the radiation therapist can readily determine visually whether the extents 351 of the planned treatment beam extend beyond the surface 352 of a patient's skin for any selected treatment beam angle.

Implementation of method 500 as described above provides a match verification tool that enables fast and accurate visual confirmation that the patient is correctly positioned relative to the planned treatment isocenter, so that a planned treatment beam extends beyond the surface of the patient's skin. Furthermore, the virtual BEV image employed in the above-described match verification tool is generated without the additional dosing associated with a conventional X-ray BEV image.

The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments.

Aspects of the present embodiments may be embodied as a system, method or computer program product. Accordingly, aspects of the present disclosure may take the form of an entirely hardware embodiment, an entirely software embodiment (including firmware, resident software, microcode, etc.) or an embodiment combining software and hardware aspects that may all generally be referred to herein as a "circuit," "module" or "system." Furthermore, aspects of the present disclosure may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

We claim:

1. A computer-implemented method of viewing a planning target volume for radiation therapy, the method comprising:
   receiving a first two-dimensional (2D) view of the planning target volume based on initial digital volume data, wherein the first 2D view has a first image plane that is perpendicular to a planned treatment beam path that passes through the first image plane;
   acquiring time-of-treatment digital volume data of the planning target volume;
   generating a second 2D view of the planning target volume based on the acquired time-of-treatment digital volume data, wherein the second 2D view has a second image plane that is coincident with the first image plane;
   based on the second 2D view of the planning target volume, determining field outlines of a treatment beam associated with the planning target volume; and
   causing the second 2D view to be displayed with the field outlines of the treatment beam overlaying the second 2D view.

2. The computer-implemented method of claim 1, wherein the first 2D view comprises one of a virtual slice disposed along the planned treatment beam path and a projected beam's-eye view of the planning target volume.

3. The computer-implemented method of claim 1, wherein causing the first 2D view to be displayed with the field outlines of the treatment beam overlaying the second 2D view comprises causing the first 2D view and the second 2D view to be displayed in a blended view.

4. The computer-implemented method of claim 3, further comprising, overlaying anatomical structures associated with the planning target volume on the blended view.

5. The computer-implemented method of claim 1, further comprising, overlaying anatomical structures associated with the planning target volume on the second 2D view.

6. The computer-implemented method of claim 1, wherein the initial digital volume data includes a set of X-ray images of the planning target volume generated via cone-beam commuted tomography.

7. The computer-implemented method of claim 1, wherein the initial digital volume data are generated prior to the planning target volume being positioned for the acquisition of the time-of-treatment digital volume data.

8. The computer-implemented method of claim 1, wherein the planned treatment beam path is parallel to a line between a point of view of the first 2D view and the image plane of the first 2D view.

9. The computer-implemented method of claim 1, further comprising:
   determining a set of field outlines of the treatment beam with respect to a third 2D view of the planning target volume that has a third image plane that is parallel to one of an axial, a sagittal, and a coronal plane; and
   causing the third 2D view to be displayed with the set of field outlines of the treatment beam overlaying the third 2D view.

10. The computer-implemented method of claim 1, wherein the time-of-treatment digital volume data comprise a digital volume of the planning target volume generated by cone-beam computed tomography.

11. The computer-implemented method of claim 1, further comprising:
    generating a third 2D view of the planning target volume based on the acquired time-of-treatment digital volume data, wherein the third 2D view has a third image plane that is 1) perpendicular to a planned treatment beam path that passes through the third image plane and 2) not parallel to the first image plane;
    based on the third 2D view of the planning target volume, determining field outlines of the treatment beam associated with the planning target volume; and
    causing the third 2D view to be displayed with the field outlines of the treatment beam overlaying the third 2D view.

12. A computer-implemented method of viewing a planning target volume for radiation therapy, the method comprising:
    receiving initial digital volume data of the planning target volume;
    generating a first 2D view of the planning target volume based on the initial digital volume data, wherein the first 2D view has a first image plane that is perpendicular to a planned treatment beam path that passes through the first image plane;
    acquiring time-of-treatment digital volume data of the planning target volume;
    generating a second 2D view of the planning target volume based on the acquired time-of-treatment digital volume data, wherein the second 2D view has a second image plane that is coincident with the first image plane;
    based on the second 2D view of the planning target volume, determining field outlines of a treatment beam associated with the planning target volume; and
    causing the second 2D view to be displayed with the field outlines of the treatment beam overlaying the second 2D view.

13. The computer-implemented method of claim 12, wherein the first 2D view comprises one of a virtual slice disposed along the planned treatment beam path and a projected beam's-eye view of the planning target volume.

14. The computer-implemented method of claim 12, wherein causing the first 2D view to be displayed with the field outlines of the treatment beam overlaying the second 2D view comprises causing the first 2D view and the second 2D view to be displayed in a blended view.

15. The computer-implemented method of claim 12, further comprising, overlaying anatomical structures associated with the planning target volume on the second 2D view.

16. The computer-implemented method of claim 12, wherein the initial digital volume data includes a set of X-ray images of the planning target volume generated via cone-beam computed tomography.

17. The computer-implemented method of claim 12, wherein the initial digital volume data are generated prior to the planning target volume being positioned for the acquisition of the time-of-treatment digital volume data.

18. The computer-implemented method of claim 12, wherein the planned treatment beam path is parallel to a line between a point of view of the first 2D view and the image plane of the first 2D view.

19. The computer-implemented method of claim 12, wherein the initial digital volume data comprise a digital volume of the planning target volume generated by cone-beam computed tomography.

20. The computer-implemented method of claim 12, wherein the time-of-treatment digital volume data comprise a digital volume of the planning target volume generated by cone-beam computed tomography.

\* \* \* \* \*